(12) United States Patent
Dubois

(10) Patent No.: US 6,833,474 B2
(45) Date of Patent: Dec. 21, 2004

(54) PROCESS FOR MANUFACTURING ACRYLIC ACID FROM PROPANE IN THE ABSENCE OF MOLECULAR OXYGEN

(75) Inventor: Jean-Luc Dubois, Millery (FR)

(73) Assignee: ARKEMA, Puteaux (FR)

( * ) Notice: Subject to any disclaimer, the term of this patent is extended or adjusted under 35 U.S.C. 154(b) by 0 days.

(21) Appl. No.: 10/093,265

(22) Filed: Mar. 7, 2002

(65) Prior Publication Data

US 2003/0088124 A1 May 8, 2003

(30) Foreign Application Priority Data

Mar. 7, 2001 (FR) .............................. 01 03106

(51) Int. Cl.$^7$ ............................................. C07C 51/16
(52) U.S. Cl. ...................... 562/549; 562/542; 562/545; 562/547
(58) Field of Search ............................. 562/542, 545, 562/547, 549, 532

(56) References Cited

U.S. PATENT DOCUMENTS

| | | | | |
|---|---|---|---|---|
| 3,903,149 A | * | 9/1975 | Kadowaki et al. ........... | 562/549 |
| 4,260,822 A | * | 4/1981 | Krieger et al. .............. | 562/549 |
| 4,341,717 A | * | 7/1982 | Callahan et al. ............ | 558/324 |
| 5,198,580 A | * | 3/1993 | Bartek et al. ............... | 562/542 |
| 5,330,954 A | | 7/1994 | Cadot et al. | |
| 5,498,588 A | * | 3/1996 | Brazdil et al. .............. | 502/353 |
| 5,780,700 A | | 7/1998 | Hagemeyer et al. | |
| 5,994,580 A | * | 11/1999 | Takahashi et al. .......... | 562/549 |
| 6,025,523 A | | 2/2000 | Hecquet et al. | |
| 6,080,893 A | | 6/2000 | Hecquet et al. | |

FOREIGN PATENT DOCUMENTS

| | | |
|---|---|---|
| EP | 0603836 | 6/1994 |
| EP | 0895809 | 2/1999 |
| EP | 0895809 | * 10/1999 |
| WO | WO 99/03809 | 1/1999 |
| WO | WO 00/10959 | 3/2000 |

OTHER PUBLICATIONS

European Search Report of App. No. FA 603915 and FR 0103106, completed Dec. 6, 2001.

* cited by examiner

Primary Examiner—Cecilia J. Tsang
Assistant Examiner—Taylor V. Oh
(74) Attorney, Agent, or Firm—Millen White Zelano & Branigan, P.C.

(57) ABSTRACT

The invention relates to a process for manufacturing acrylic acid from propane.

According to this process, a gas mixture, which is free from molecular oxygen and comprises propane, steam as well as, optionally, an inert gas, is passed over a solid composition of formula (I)

$$Mo_1V_aTe_bNb_cSi_dO_x \quad (I)$$

in which:
   a is between 0.006 and 1, including the end points;
   b is between 0.006 and 1, including the end points;
   c is between 0.006 and 1, including the end points;
   d is between 0 and 3.5, including the end points; and
   x is the quantity of oxygen bound to the other elements, and depends on their oxidation states,
in order to oxidize the propane according to the following redox reaction (1):

$$SOLID_{oxidized} + PROPANE \rightarrow SOLID_{reduced} + ACRYLIC\ ACID \quad (1).$$

25 Claims, No Drawings

PROCESS FOR MANUFACTURING ACRYLIC ACID FROM PROPANE IN THE ABSENCE OF MOLECULAR OXYGEN

CROSS-REFERENCE TO RELATED APPLICATIONS

This application claims priority to French patent application number 01 03 106 filed Mar. 7, 2001.

The present invention concerns production of acrylic acid from propane in the absence of molecular oxygen.

It is known from European Patent Application No. EP-A-608838 to prepare an unsaturated carboxylic acid from an alkane according to a vapour-phase catalytic oxidation reaction in the presence of a catalyst containing a mixed metal oxide comprising, as essential components, Mo, V, Te, O as well as at least one element selected from the group consisting of niobium, tantalum, tungsten, titanium, aluminium, zirconium, chromium, manganese, iron, ruthenium, cobalt, rhodium, nickel, palladium, platinum, antimony, bismuth, boron, indium and cerium, these elements being present in well-specified proportions. The uses of such a silicon-free catalyst, which are described in the examples of this document, lead to good selectivities for acrylic acid, but they are implemented in the presence of air.

The European Patent Application No. EP-A-895809 describes catalysts based on oxides comprising molybdenum, vanadium, niobium, oxygen, tellurium and/or antimony, as well as at least one other element such as iron or aluminium. These catalysts can be used for the conversion of propane into acrylic acid, but only conversion in the presence of molecular oxygen is envisaged. They may also comprise a support such as silica, although the only examples of this document relating to the production of acrylic acid, namely Examples 9 and 10, implement silica-free catalysts.

The European Patent Application No. EP-A-603836 relates to a process for preparing a catalyst for the production of a nitrile. This catalyst may be a complex oxide comprising molybdenum, vanadium, tellurium, oxygen as well as at least one other element, which may be—among other elements—niobium or antimony. The examples of this patent application describe preparations of catalysts which furthermore contain silica.

The Japanese Patent No. JP 4235153 concerns the production of acrylonitrile from propane and ammonia, according to a redox process.

The Applicant has now discovered that acrylic acid can be manufactured by gas-phase oxidation of propane in the absence of molecular oxygen, by passing a gaseous mixture of propane and steam and, optionally, an inert gas, over a particular solid composition of mixed oxides, which acts as a redox system and provides the oxygen necessary for the reaction.

The advantages of this novel process are as follows:
the limitation of the over-oxidation of the products which are formed, which takes place in the presence of molecular oxygen; according to the present invention, because the operation is carried out in the absence of molecular oxygen, the formation of $CO_x$ (carbon monoxide and carbon dioxide), which are breakdown products, is reduced, which makes it possible to improve the selectivity for acrylic acid;
the selectivity for acrylic acid remains good when the reduction factor of the solid composition increases;
the solid composition, once it has undergone reduction and a progressive loss of its activity, can be regenerated easily by heating in the presence of oxygen, or a gas containing oxygen, after a certain period of use; after regeneration, the solid recovers its initial activity and can be used in a new reaction cycle;
the separation of the steps of reducing the solid composition and regenerating it makes it possible:
to increase the selectivity for acrylic acid;
to increase the partial pressure of propane, such a partial pressure of propane in the feed being no longer limited by the existence of an explosive zone created by the propane+oxygen mixture.

The present invention therefore relates to a process for manufacturing acrylic acid from propane, characterized in that a gas mixture, which is free from molecular oxygen and comprises propane, steam as well as, optionally, an inert gas, is passed over a solid composition of formula (I)

$$Mo_1V_aTe_bNb_cSi_dO_x \quad (I)$$

in which:
a is between 0.006 and 1, including the end points;
b is between 0.006 and 1, including the end points;
c is between 0.006 and 1, including the end points;
d is between 0 and 3.5, including the end points; and
x is the quantity of oxygen bound to the other elements, and depends on their oxidation states,
in order to oxidize the propane according to the following redox reaction (1)

$$SOLID_{oxidized}+PROPANE \rightarrow SOLID_{reduced}+ACRYLIC\ ACID \quad (1).$$

This process makes it possible to obtain a selectivity of close to 60% for acrylic acid. Furthermore, if the propylene, which is a by-product, and the unconverted propane are recycled, an overall selectivity of close to 70% is achieved.

Other characteristics and advantages of the invention will become apparent on reading the following explanation, which is illustrated by examples.

DETAILED EXPLANATION OF THE INVENTION

The catalyst used according to the invention satisfies the formula (I) indicated above.

The oxides of the various metals involved in the composition of the mixed oxide of formula (I) can be used as starting materials in the preparation of this composition, although the starting materials are not limited to the oxides; the following may be mentioned as other starting materials:
in the case of molybdenum: ammonium molybdate, ammonium paramolybdate, ammonium heptamolybdate, molybdic acid, molybdenum halides or oxyhalides such as $MoCl_5$, organometallic compounds of molybdenum, e.g. molybdenum alkoxides such as $Mo(OC_2H_5)_5$, acetylacetone molybdenyl;
in the case of vanadium: ammonium metavanadate, vanadium halides or oxyhalides such as $VCl_4$, $VCl_5$ or $VOCl_3$, organometallic compounds of vanadium, e.g. vanadium alkoxides such as $VO(OC_2H_5)_3$;
in the case of tellurium: telluric acid;
in the case of niobium: niobic acid, $Nb_2(C_2O_4)_5$, niobium tartrate; niobium hydrogen oxalate, oxotrioxalatoammonium niobate $[(NH_4)_3[NbO(C_2O_4)_3]] \cdot 1.5H_2O$, ammonium niobium oxalate, ammonium niobium tartrate, niobium halides or oxyhalides such as $NbCl_3$, $NbCl_5$ and organometallic compounds of niobium, e.g. niobium alkoxides such as $Nb(OC_2H_5)_5$, $Nb(O-n-Bu)_5$; and, in general, all the compounds capable of forming an oxide by calcination, namely the metal salts of organic acids, the metal salts of inorganic acids, metal complex compounds, etc.

The source of silicon generally consists of colloidal silica.

According to particular embodiments, the solid compositions of formula (I) may be prepared by mixing, while stirring, aqueous solutions of niobic acid, ammonium heptamolybdate, ammonium metavanadate and telluric acid, preferably while adding colloidal silica, then pre-calcining under air at about 300° C. and calcining under nitrogen at about 600° C.

Preferably, in the solid composition of formula (I):

a is between 0.09 and 0.8, including the end points;

b is between 0.04 and 0.6, including the end points;

c is between 0.01 and 0.4, including the end points; and d is between 0.4 and 1.6, including the end points.

According to the invention, acrylic acid is manufactured by passing a gas mixture, which is free from molecular oxygen and comprises propane and steam as well as, optionally, an inert gas, over a solid composition of formula (I) as defined above, in order to carry out the redox reaction (1) as indicated above.

Generally, the redox reaction (1) is carried out at a temperature of 200 to 500° C., preferably 250 to 450° C., and even more preferably 350 to 400° C.

The pressure is generally from $1.01 \times 10^4$ to $1.01 \times 10^6$ Pa (0.1 to 10 atmospheres), preferably from $5.05 \times 10^4$ to $5.05 \times 10^5$ Pa (0.5–5 atmospheres).

The residence time is generally from 0.01 to 90 seconds, preferably from 0.1 to 30 seconds.

The volume ratio of propane/steam in the gas phase is not critical, and may vary in wide limits.

Similarly, the proportion of inert gas, which may be helium, krypton, a mixture of these two gases, or alternatively nitrogen, carbon dioxide, etc., is not critical either, and may also vary in wide limits.

As an order of magnitude for the proportions of the initial mixture, the following ratio (by volume) may be mentioned:

propane/inert (He—Kr)/$H_2O$ (steam): 10–20/40–50/40–50

During the redox reaction (1), the solid composition undergoes reduction and a progressive loss of its activity. This is why, once the solid composition has been converted at least partially into the reduced state, regeneration of the said solid composition is carried out according to the reaction (2):

$$SOLID_{reduced} + O_2 \rightarrow SOLID_{oxidized} \quad (2)$$

by heating in the presence of oxygen, or a gas containing oxygen, at a temperature of 250 to 500° C. for the time needed to re-oxidize the solid composition.

Generally, the process is implemented until the reduction factor of the solid composition is between 10 and 40%.

This reduction factor may be monitored during the reaction via the quantity of products obtained. The equivalent quantity of oxygen is then calculated. It may also be followed via the exothermicity of the reaction.

After the regeneration, which may be carried out under temperature and pressure conditions identical to, or different from, those of the redox reaction, the solid composition recovers an initial activity and can be used in a new reaction cycle.

The redox reaction (1) and the regeneration may be carried out in a conventional reactor, such as a fixed-bed reactor, a fluidized-bed reactor or a transported-bed reactor.

The redox reaction (1) and the regeneration may therefore be carried out in a device with two stages, namely a reactor and a regenerator which operate simultaneously, and in which two batches of solid composition alternate periodically; the redox reaction (1) and the regeneration may also be carried out in the same reactor, by alternating the periods of reaction and regeneration.

Preferably, the redox reaction (1) and the regeneration are carried out in a reactor with a transported catalyst bed.

It is possible to use an operating mode with a single pass or with recycling.

According to a preferred embodiment, the propylene which is produced as a by-product, and/or the propane which has not reacted, are recycled (or returned) to the inlet of the reactor, that is to say they are re-introduced at the inlet of the reactor, mixed together with, or in parallel with, the initial mixture of propane, steam and, optionally, inert gas(es).

EXAMPLES

The following examples illustrate the present invention without, however, limiting its scope.

In the formulae indicated in Examples 1 and 2, x is the quantity of oxygen bound to the other elements, and depends on their oxidation states.

The conversions, selectivities and yields are defined as follows:

$$\text{Conversion (\%) of the propane} = \frac{\text{number of moles of propane having reacted}}{\text{number of moles of propane introduced}} \times 100$$

$$\text{Selectivity (\%) for acrylic acid} = \frac{\text{number of moles of acrylic acid formed}}{\text{number of moles of propane having reacted}} \times 100$$

$$\text{Yield (\%) for acrylic acid} = \frac{\text{number of moles of acrylic acid formed}}{\text{number of moles of propane introduced}} \times 100$$

The selectivities and yields relating to the other compounds are calculated in a similar way.

Example 1

Preparation of the Catalyst A of Formula

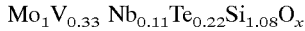

$Mo_1V_{0.33}Nb_{0.11}Te_{0.22}Si_{1.08}O_x$ a) Preparation of a Niobium Solution A 600 ml beaker is filled with 80 g of distilled water then 6.4 g (0.038 mole) of niobic acid. 12.9 g (0.102 mole) of oxalic acid dihydrate are then added.

The molar ratio of oxalic acid/niobium is therefore 2.69.

The solution obtained previously is heated to 60° C. for 2 hours and 19 minutes, while stirring and covering to prevent evaporation. A white suspension is thus obtained, which is allowed to cool to 30° C. while stirring, which takes about 2 hours.

b) Preparation of a Solution of Mo, V and Te

A 600 ml beaker is filled with 265 g of distilled water, 61 g (0.346 mole) of ammonium heptamolybdate, 13.3 g (0.114 mole) of ammonium metavanadate $NH_4VO_3$ and 17.4 g (0.076 mole) of telluric acid [supplier: FLUKA].

The solution obtained previously is heated to 60° C. for 1 hour and 35 minutes, while stirring and covering to prevent evaporation. A clear red solution is thus obtained, which is allowed to cool to 30° C. while stirring, which takes about 2 hours.

c) Introduction of the Silica 56 g of Ludox silica (containing 40% by weight of silica, supplied by the company Dupont) are added to 56 g of distilled water. The solution with 20% by weight of silica which is obtained is then added, while stirring, to the solution of Mo, V and Te prepared previously. The latter retains its clarity and its red colour.

The niobium solution prepared previously is then added. A fluorescent-orange gel is thus obtained after several minutes of stirring. This solution is then put in the oven at 130° C. overnight.

114.9 g of precursor is thus recovered, which is in the form of a dry product, containing 0.373 mole of Si, which corresponds to a silicon oxide mass percentage of 22.2%.

d) Calcining 30 g of the precursor obtained previously is first pre-calcined for 4 hours at 300° C. under an air flow of 48.2 ml/min/g of precursor. The solid which is obtained is then calcined for 2 hours at 600° C. under a nitrogen flow of 48.1 ml/min/g of solid.

24.9 g of catalyst A are thus obtained.

Example 2

Preparation of the Catalyst B of Formula

$Mo_1V_{0.33}Nb_{0.11}Te_{0.22}O_x$

The procedure carried out is as indicated in parts a) and b) of Example 1.

The niobium solution is then added to the solution of Mo, V and Te. A fluorescent-orange gel is thus obtained after several minutes of stirring. This solution is then put in the oven at 130° C. overnight.

88.8 g of precursor is thus recovered.

The procedure then carried out is as indicated in part d) of Example 1.

20.8 g of catalyst B are thus obtained.

Example 3

Tests of the Catalyst A a) Tests in Pulsed Mode a1) Operating Mode

Details of the operating mode implemented are given below.

A vertical reactor is loaded, from the bottom upwards, with a first height of 2 ml (2.346 g) of silicon carbide in the form of particles with a diameter of 1.19 mm (screening between 1 and 1.25 mm), a second height of 5 ml (5.458 g) of catalyst in the form of 0.25 to 1 mm particles, then a third height of the same silicon carbide as before (19.547 g).

The reactor is then heated to 250° C. and the vaporizer to 200° C. The electrical priming of the water pump is activated.

Once the reactor and the vaporizer have reached the temperatures indicated above, the water pump is activated and the temperature of the reactor is raised to 350° C. The temperature of the reactor is subsequently raised further to 380° C. in increments of 10° C., each increment lasting 10 minutes.

The reactor is then allowed to stabilize for 30 minutes.

The oxygen is then introduced in 10 pulses, each of 23 seconds, in order to oxidize the catalyst thoroughly. The catalyst is regarded as being fully oxidized when the temperature of the hot point has stabilized, that is to say when there is no longer any exothermicity due to the reaction (by following the temperature of the catalyst, measured by using a thermocouple placed in the catalytic bed, it is possible to see the fluctuations in temperature as a function of the pulses).

The pressure at the inlet of the reactor was about 1.1 bar, and the pressure loss through the reactor is about 0.1 bar.

As regards the actual production of acrylic acid, a redox programme is made of 60 redox cycles. A redox cycle represents:

13 seconds of propane in a continuous helium-krypton/water flow, 45 seconds of continuous helium-krypton/water flow, 20 seconds of oxygen in a continuous helium-krypton/water flow, 45 seconds of continuous helium-krypton/water flow.

Four samples are taken during the programme, each representing 15 cycles. 4 gas samples are also taken using gas bags, each sample representing about 15 cycles, or only 13 or 14 cycles in the case of the last bag. (The gas samples are taken over a period corresponding to a multiple of the duration of a cycle, so that the theoretical quantity of propane injected can be known).

Each small wash bottle (having a capacity of 25 ml and filled with 20 ml of water) is equipped with a gas bag, and when the bottle is connected to the outlet of the reactor (as soon as the liquid bubbles), the bag is opened and the stopwatch is started. A cycle lasts 133 seconds, and the programme consequently has a duration of 2 hours and 13 minutes.

In order to check the oxidation state of the catalyst, a new series of 10 23-second oxygen pulses is carried out. It shows that the oxidation state of the solid was maintained during the programme.

The reduction factor reached corresponds to a 10% reduction of the surface oxygen, for a solid catalyst having a mass-based specific surface of 10m²/g.

The liquid effluents are analysed on an HP 6890 chromatograph, after specific calibration has been carried out.

The gases are analysed during the programme on a micro-GC Chrompack chromatograph.

An acidity titration is carried out on the mixture of bottles at the end of operation, in order to determine the exact number of moles of acid produced during the programme and to validate the chromatography results.

a2) Results

In order to study the performance of the catalyst over time, a series of tests carried out under the same conditions was performed over several days.

The catalyst underwent 10 tests in pulsed mode, which makes it possible to conclude that the catalyst remained in contact with propane for 130 minutes, as a cumulative time over 600 pulses.

Between each pulsed-mode programme, a series of 1023-second oxygen pulses is carried out, so that the catalyst can remain oxidized. Taking into account the duration of the programmes, the re-oxidation series and the temperature stabilization, the catalyst remained at 380° C. for about 40 hours.

The tests T1, T2, T3, T4 and T5 were performed as explained above, that is to say:

the 60-cycle programme is divided into four 15-cycle parts;

4 small 25-ml wash bottles are used to recover the liquid effluents from each of the 15-cycle series; chromatography analysis is carried out on each bottle. A chemical acidity titration is performed on all the effluents recovered (mixture of all 4 bottles);

4 gas analyses are carried out over the entire duration of the programme; the gas is sampled for 15 cycles. There is therefore one gas sample per small wash bottle.

There are thus 4 liquid+gas samples during the programmes. The results presented in the table, and on the graph, correspond to the average of the results of the 4 parts (bottles and gas).

The programmes B1, B2, B3, B4 and B5 were carried out slightly differently:

For all the tests, the levels determined by chromatography are correct since they were confirmed by the chemical acid titration in the recovered liquid effluents.

The results are reported in Table 1 below, in which:

AA denotes acrylic acid;

acA denotes acetic acid;

$CO_x$ denotes carbon oxides;

UCF denotes the unitary conversion factor (or yield).

| TEST | T1 | B1 | T2 | T3 | B2 | B3 | T4 | B4 | T5 | B5 |
|---|---|---|---|---|---|---|---|---|---|---|
| Cumulative time under propane (min) | 10(13)[7] | 20(26) | 30(39) | 40(52) | 50(65) | 60(78) | 70(91) | 80(104) | 90(117) | 100(130) |
| Hot point (° C.) | | | | | 383.7 to 384.5 | | | | | |
| Carbon balance (%) | 98.1 | 103.1 | 100.7 | 96.5 | 98.1 | 101.1 | 98.8 | 102.9 | 98.9 | 108.0[8] |
| Propane Conversion (%)[9] | 16.8 | 17.2 | 16.8 | 16.6 | 15.7 | 17.4 | 16.6 | 17.9 | 16.8 | 18 |
| Acidity: chromatography (moles) | $9.1 \times 10^{-4}$ | $10.3 \times 10^{-4}$ | $9.6 \times 10^{-4}$ | $9.8 \times 10^{-4}$ | $8.9 \times 10^{-4}$ | $9.6 \times 10^{-4}$ | $9.7 \times 10^{-4}$ | $10.6 \times 10^{-4}$ | $9.9 \times 10^{-4}$ | $10.5 \times 10^{-4}$ |
| Acidity: chemical titration (moles) | $9.4 \times 10^{-4}$ | $9.7 \times 10^{-4}$ | $9.4 \times 10^{-4}$ | $9.4 \times 10^{-4}$ | $8.6 \times 10^{-4}$ | $9.9 \times 10^{-4}$ | $9.3 \times 10^{-4}$ | $10.3 \times 10^{-4}$ | $9.3 \times 10^{-4}$ | $10.1 \times 10^{-4}$ |
| Acrylic acid yield (%) | 9.6 | 9.7 | 9.5 | 9.5 | 8.6 | 10.0 | 9.3 | 10.4 | 9.3 | 10.1 |
| Acetic acid yield (%) | 1.1 | 1.2 | 1.1 | 1.1 | 1.0 | 1.2 | 1.1 | 1.2 | 1.2 | 1.2 |
| Propylene yield (%) | 3.0 | 3.0 | 3.0 | 2.8 | 2.9 | 3.0 | 2.9 | 3.0 | 2.9 | 3.1 |
| Yield of Useful products[10] (%) | 13.9 | 14.4 | 13.8 | 13.6 | 12.7 | 14.4 | 13.5 | 14.8 | 13.6 | 14.6 |
| $CO_x$ yield (%) | 2.8 | 2.8 | 2.9 | 2.9 | 2.9 | 2.9 | 3.0 | 3.0 | 3.1 | 3.3 |
| Selectivity for Acrylic acid (%)[11] | 57.3 | 56.4 | 56.9 | 57.2 | 54.7 | 57.7 | 56.2 | 58 | 55.6 | 56 |
| Selectivity for Acetic acid (%) | 6.4 | 7.1 | 6.4 | 6.8 | 6.5 | 6.7 | 6.9 | 6.7 | 7.1 | 6.8 |
| Selectivity for Propylene (%) | 18 | 17.7 | 17.9 | 16.9 | 18.5 | 17.2 | 17.3 | 16.8 | 17.1 | 17.3 |
| Selectivity for Useful products (%) | 82.6 | 82.5 | 82.4 | 82.2 | 80.8 | 82.8 | 81.7 | 82.8 | 81.1 | 81.3 |
| Selectivity for $CO_x$ (%) | 16.8 | 17.1 | 17.1 | 17.4 | 18.8 | 16.8 | 18.0 | 16.7 | 18.5 | 18.3 |
| Moles of oxygen consumed[12] | $5.8 \times 10^{-3}$ | $6.04 \times 10^{-3}$ | $5.9 \times 10^{-3}$ | $5.9 \times 10^{-3}$ | $5.6 \times 10^{-3}$ | $6.1 \times 10^{-3}$ | $5.9 \times 10^{-3}$ | $6.3 \times 10^{-3}$ | $6.0 \times 10^{-3}$ | $6.6 \times 10^{-3}$ |
| AA productivity[13] | 0.676 | 0.687 | 0.675 | 0.671 | 0.611 | 0.710 | 0.659 | 0.734 | 0.657 | 0.717 |
| AcA productivity In moles/kg of catalyst/hr | 0.113 | 0.129 | 0.114 | 0.120 | 0.108 | 0.123 | 0.121 | 0.128 | 0.125 | 0.130 |

[7]In theory, the propane pulse is 10 s. In practice, it lasts 13 s. The first value corresponds to theory, i.e. to a 10-second pulse, and the second value shown in brackets corresponds to a 13 s pulse.
[8]The carbon balance is a surplus. Probable error in the gas analysis, since the bag was porous.
[9]Propane conversion = sum of the UCFs
[10]Products used: acrylic acid, acetic acid, acrolein, acetaldehyde, acetone and propylene
[11]The selectivities are determined by taking: product UCF/Σ UCF
[12]The number of moles of $O_2$ consumed is calculated on the basis of the products formed
[13]In redox mode, the productivity is calculated while taking account of the duration of the propane pulse (13 s)

the liquid effluents were recovered over the entire duration of the programme in a large 125-ml bottle; a chromatography analysis and a chemical acidity titration are carried out on this bottle;

a single 15-cycle gas sample is taken during the programme.

A liquid analysis of the entire programme and a gas analysis of a part of the programme are thus carried out for these tests. The results are therefore slightly less precise, which may explain why the carbon balances are slightly inferior.

It can be seen that the catalyst remained stable over the course of the tests, while giving substantially identical results in each test.

The results are very good, the selectivity for acrylic acid (AA) being close to 60% (it varies from 55% to 58% over the 10 tests) and that for propylene (Pen) being 17.5%.

The conversion of the propane (Pan) is 17% on average; it varies from 16 to 18% during the experiment. It is determined by taking the sum of the product UCFs.

Furthermore, the reactor was found to be clean after removal of the catalyst, that is to say there was no black deposit at the outlet of the reactor, in contrast to what happened during the standard co-fed tests.

b) Tests in Co-fed Mode

These tests are conventional, that is to say they conform with the known processes. They were carried out only for purposes of comparison.

Air was used instead of the krypton-helium mixture, in order to provide molecular oxygen, and the feed therefore consisted of a mixture of propane, air and steam.

The pressure at the inlet of the reactor was about 1.15 bar, and the pressure loss through the reactor was about 0.15 bar.

The mass of catalyst loaded was 4.872 g, which equated to a height of 5 ml in the reactor.

The results and the operating conditions are reported in Table 2 below, in which:

SV denotes hourly space velocity;

AA and acA, $CO_x$ and UCF have the same meanings as in Table 1.

| TEST | T6 | T7 |
|---|---|---|
| Mode | Co-fed | Co-fed |
| Propane/Air/$H_2O$ (by volume) | 9.1/45.5/45.5 | 9.1/45.4/45.5 |
| SV ($h^{-1}$) | 1730 | 1730 |
| Reaction temperature (° C.) | 390 | 400 |
| Hot point (° C.) | 408–411 | 431 |
| Duration of the programme (h) after 1 hr 30 min of stabilization | 1 hr 00 | 1 hr 00 |
| Carbon balance (%) | 105.2 | 102.4 |
| Propane Conversion (%)[9] | 22.2 | 31.2 |
| Acidity: chromatography (moles) | n.d. | 52.1 × $10^{-4}$ |
| Acidity: chemical titration (moles) | n.d. | 53.8 × $10^{-4}$ |
| Acrylic acid yield (%) | 11.0 | 12.2 |
| Acetic acid yield (%) | 1.0 | 1.8 |
| Propylene yield (%) | 3.9 | 3.78 |
| Yield of Useful products (%) | 16.0 | 17.88 |
| $CO_x$ yields (%) | 6.1 | 13.34 |
| Selectivity for Acrylic acid (%) | 49.6 | 39.0 |
| Selectivity for Acetic acid (%) | 4.2 | 5.8 |
| Selectivity for Propylene (%) | 17.6 | 12.1 |
| Selectivity for Useful products[14] (%) | 72.2 | 57.2 |
| Selectivity for $CO_x$ (%) | 27.5 | 42.7 |
| AA productivity[15] | 0.796 | 0.882 |
| acA productivity in moles/kg of catalyst/hr | 0.072 | 0.194 |

[9]Propane conversion = sum of the UCFs
[14]Useful products: acrylic acid, acetic acid, acrolein, acetaldehyde, acetone and propylene
[15]In redox mode, the productivity is calculated while taking account of the duration of the propane pulse (13 s)

By comparing the results of Table 1 (invention) with those of Table 2 (prior art), it can therefore be seen that at low conversion (17 to 22%), the selectivity for acrylic acid is 8% more in pulsed mode than in co-fed mode, and the selectivity for useful products is 10% higher.

At higher temperature, in co-fed mode (right-hand column of Table 2), the conversion of the propane increases, but the selectivity for acrylic acid falls, and that for carbon oxides $CO_x$ increases.

Example 4

Tests of the Catalyst B

Tests were carried out on the catalyst B as indicated in Example 3, in co-fed mode and in pulsed mode.

The quantity of silicon carbide loaded first (first height) was 2.44 g, the quantity of the catalyst B (second height) was 5.676 g and the quantity of silicon carbide (third height) was 19.617 g.

The sizes of the silicon-carbide and catalyst particles were identical to those in Example 3.

Furthermore, in order to ascertain whether it is possible to recycle the propylene which is produced, various proportions of propylene were added to the propane during the pulsed-mode operation, instead of recycling the propylene which was produced.

A propylene flow rate was therefore added to the constant propane flow rate, every 15 cycles, in the following proportions:

100% of propane—0% of propylene for 15 cycles
100% of propane—10% of propylene for 15 cycles
100% of propane—20% of propylene for 15 cycles
100% of propane—34% of propylene for 15 cycles It can be seen that the re-injected propylene is almost fully converted. The temperature of 360° C. seems to be too high for the propylene, since the $CO_x$ yields increase following the increase in the propylene flow rate.

The same procedure as before was then carried out, but at a temperature of 340° C.

The pressure at the inlet of the reactor was about 1.1 bar, and the pressure loss through the reactor was about 0.1 bar.

The reduction factor of the catalyst after the oxidation of the propane was between 10 and 40% of the surface oxygen, depending on the temperature and the content of propylene.

The yields are not quite as high, but the selectivities remain of the same order of magnitude as at 360° C. A decrease in the selectivity for acrylic acid is also observed, in favour of the increase in the selectivities for $CO_x$ and acetic acid. Compared with the test at 360° C., an increase in the selectivity for acetone is noted.

The same procedure is then carried out again, but at a temperature of 320° C.

The pressure at the inlet of the reactor was about 1.1 bar, and the pressure loss through the reactor was about 0.1 bar.

As regards the yields and selectivities, the same comment as before can be made. Furthermore, it is observed that the reaction temperature is no longer high enough to convert the propane correctly, which explains the low product yields, in particular during the first 15 cycles, in which no propylene is added. For the subsequent cycles, the increase in the product yields is mainly due to the conversion of the propylene.

The results of the tests at 320° C., 340° C. and 360° C. are compiled in Table 3 below, in which:

Pen denotes propylene;

AA and acA, $CO_x$, UCF and SV have the same meanings as in Tables 1 and 2.

| TESTS | T8 | | | | T9 | | | | T10 | | | |
|---|---|---|---|---|---|---|---|---|---|---|---|---|
| Pan-Pen or $O_2$/He-Kr/$H_2O$[19] | 10-0 to 3.4[19] or 20/45/45 | | | | 10-0 to 3.4 or 20/45/45 | | | | 10-0 to 3.4 or 20/45/45 | | | |
| Reaction temperature (° C.) | 360 | | | | 340 | | | | 320 | | | |
| Hot point (° C.) | 364.4 to 368.9 | | | | 343.9 to 347.8 | | | | 323.4 to 326.7 | | | |
| Duration of the programme (h) | 2 hr 13 min | | | | 2 hr 13 min | | | | 2 hr 13 min | | | |
| Bottle No (15 cycles per bottle) | 1 | 2 | 3 | 4 | 1 | 2 | 3 | 4 | 1 | 2 | 3 | 4 |
| Carbon balance (%) | 101 | 104 | 104 | 107 | 99 | 107 | 110 | 108 | 90 | 96 | 101 | 109 |
| Propane Conversion (%) | 21.1 | 11.2 | 12.6 | 13.4 | 14.9 | 0.5 | 1.4 | 6.2 | 22.0 | 7.6 | 7.2 | 2.2 |
| Propylene Conversion (%) | 0 | 97.1 | 96.9 | 97.0 | 0 | 96.7 | 95.4 | 96.0 | 0 | 97.0 | 95.0 | 94.5 |
| Selectivity for Acrylic acid (%) | 44.4 | 46.2 | 39.8 | 34.9 | 39.7 | 43.2 | 31.0 | 34.3 | 35.1 | 33.8 | 31.5 | 30.7 |
| Selectivity for Acetic acid (%) | 20.4 | 19.2 | 24.2 | 28.7 | 19.1 | 20.5 | 29.5 | 29.5 | 20.9 | 22.4 | 25.8 | 27.5 |
| Selectivity for Propylene (%) | 11.5 | 9.45 | 7.2 | 5.4 | 15.4 | 11.5 | 8.0 | 6.1 | 16.1 | 12.8 | 7.9 | 6.5 |
| Selectivity for Useful products (%)[17] | 78.1 | 77.0 | 73.5 | 71.4 | 77.3 | 80.1 | 74.9 | 76 | 79.8 | 77.7 | 77.6 | 79.1 |
| Selectivity for $CO_x$ (%) | 21.3 | 22.4 | 25.8 | 28.0 | 20.6 | 18.7 | 23.5 | 22.5 | 18.5 | 20.6 | 20.1 | 18.2 |
| AA productivity | 0.752 | | | | 0.562 | | | | 0.426 | | | |
| acA productivity in moles/kg of catalyst/hr[18] | 0.682 | | | | 0.630 | | | | 0.513 | | | |

[17]Useful products: acrylic acid, acetic acid, acrolein, acetaldehyde, acetone and propylene
[18]In redox mode, the productivity is calculated while taking account of the duration of the propane pulse (13 s)
[19]A propylene flow rate is added, in the following proportions, to the constant propane flow rate every 15 cycles:
100% Pan - 0% Pen for 15 cycles
100% Pan - 10% Pen for 15 cycles
100% Pan - 20% Pen for 15 cycles
100% Pan - 30% Pen for 15 cycles Thus, whatever the reaction temperature (320° C., 340° C. or 360° C.), all the added propylene is converted. The outgoing propylene is therefore regarded as being a product, and not a reactant.

What is claimed is:

1. A process for manufacturing acrylic acid from propane, comprising passing a gas mixture comprising propane and steam, as well as, optionally, an inert gas, over a solid composition of formula (I)

$$Mo_1V_aTe_bNb_cSi_dO_x \qquad (I)$$

in which:
 a is between 0.006–1;
 b is between 0.006–1;
 c is between 0.006–1;
 d is between 0–3.5; and
 x is the quantity of oxygen bound to the other elements, and depends on their oxidation states,
 with the proviso that the gas mixture is free from molecular oxygen.

2. A process according to claim 1, wherein, in the solid composition of formula (I):
 a is 0.09–0.8;
 b is 0.04–0.6;
 c is 0.01–0.4; and
 d is 0.4–1.6.

3. A process according to claim 1, wherein the reaction is carried out at a temperature of 200–500° C.

4. A process according to claim 3, wherein the reaction is carried out at a temperature of 250–450° C.

5. A process according to claim 1, wherein the reaction is carried out under a pressure of $1.01 \times 10^4$–$1.01 \times 10^6$ Pa.

6. A process according to claim 5, wherein the reaction is carried out under a pressure of $5.05 \times 10^4$–$5.05 \times 10^5$ Pa.

7. A process according to claim 1, wherein the reaction is carried out with a residence time of 0.01–90 seconds.

8. A process according to claim 7, wherein the reaction is carried out with a residence time of 0.1–30 seconds.

9. A process according to claim 2, wherein the reaction is carried out at a temperature of 250–450° C., under a pressure of $5.05 \times 10^4$–$5.05 \times 10^5$ Pa and with a residence time of 0.1–30 seconds.

10. A process according to claim 1, further comprising implemented with a reduction factor of between 10–40% for the solid composition.

11. A process according to claim 9, further comprising implemented with a reduction factor of between 10–40% for the solid composition.

12. A process according to claim 1, wherein once the solid composition has been converted at least partially into the reduced state, further comprising regeneration the solid composition:
 by heating in the presence of oxygen, or a gas containing oxygen, at a temperature of 250–500° C. for the time needed to re-oxidize the solid composition.

13. A process according to claim 10, wherein once the solid composition has been converted at least partially into the reduced state, further comprising regeneration the solid composition:
 by heating in the presence of oxygen, or a gas containing oxygen, at a temperature of 250–500° C. for the time needed to re-oxidize the solid composition.

14. A process according to claim 11, wherein once the solid composition has been converted at least partially into the reduced state, further comprising regeneration the solid composition:
 by heating in the presence of oxygen, or a gas containing oxygen, at a temperature of 250–500° C. for the time needed to re-oxidize the solid composition.

15. A process according to claim 12, wherein the reaction and the regeneration are carried out in a device with two stages, and in which two batches of solid composition alternate periodically.

16. A process according to claim 14, wherein the reaction and the regeneration are carried out in a device with two stages, and in two batches of solid composition alternate periodically.

17. A process according to claim 12, wherein the reaction and the regeneration are carried out in the same reactor, by alternating periods of reaction and regeneration.

18. A process according to claim 14, wherein the reaction and the regeneration are carried out in the same reactor, by alternating the periods of reaction and regeneration.

19. A process according to claim 12, wherein the reaction and the regeneration are carried out in a transported-bed reactor.

20. A process according to claim 1, further comprising recycling the propylene which is produced, and/or the propane which has not reacted, to the inlet of the reactor.

21. A process according to claim 15, wherein the two stages are a reactor and a regenerator which operate simultaneously.

22. A process according to claim 16, wherein the two stages are a reactor and a regenerator which operate simultaneously.

23. A process for manufacturing acrylic acid from propane, comprising passing a gas mixture comprising propane and steam, as well as, optionally, an inert gas, over a solid composition of the formula:

$$Mo_1V_{0.33}Nb_{0.11}Te_{0.22}Si_{1.08}O_x \text{ or } Mo_1V_{0.33}Nb_{0.11}Te_{0.22}O_x$$

wherein:

x is the quantity of oxygen bound to the other elements, and depends on their oxidation states, with the proviso that the gas mixture is free from molecular oxygen.

24. A process according to claim 1, wherein the process oxidizes the propane according to the following redox reaction (1):

$$SOLID_{oxidized} + PROPANE \rightarrow SOLID_{reduced} + ACRYLIC\ ACID \quad (1).$$

25. A process according to claim 12, wherein the regeneration proceeds according to the reaction (2):

$$SOLID_{reduced} + O_2 \rightarrow SOLID_{oxidized} \quad (2).$$

* * * * *

UNITED STATES PATENT AND TRADEMARK OFFICE
CERTIFICATE OF CORRECTION

PATENT NO. : 6,833,474 B2
DATED : December 21, 2004
INVENTOR(S) : Jean-Luc Dubois It is certified that error appears in the above-identified patent and that said Letters Patent is hereby corrected as shown below:

Column 12,
Lines 40 and 43, "implemented" should read -- implementing --.
Lines 47, 54 and 61, "regeneration" should read -- regenerating --.

Signed and Sealed this

Thirty-first Day of May, 2005

JON W. DUDAS
*Director of the United States Patent and Trademark Office*